United States Patent
Sherry et al.

(10) Patent No.: US 7,012,140 B1
(45) Date of Patent: Mar. 14, 2006

(54) SELECTION OF COORDINATION GEOMETRY TO ADJUST WATER EXCHANGE RATES OF PARAMAGNETIC METAL ION-BASED MACROCYCLIC CONTRAST AGENTS

(75) Inventors: A. Dean Sherry, Dallas, TX (US); Mark Woods, Dallas, TX (US); Zoltan Kovacs, Lewisville, TX (US)

(73) Assignees: Board of Regents, The University of Texas System, Austin, TX (US); Macrocyclics, Dallas, TX (US)

( * ) Notice: Subject to any disclaimer, the term of this patent is extended or adjusted under 35 U.S.C. 154(b) by 229 days.

(21) Appl. No.: 10/619,362

(22) Filed: Jul. 14, 2003

(51) Int. Cl.
C07D 255/02 (2006.01)
C07D 257/02 (2006.01)
C07D 259/00 (2006.01)

(52) U.S. Cl. ............... 540/474; 540/465; 540/470; 540/455; 540/429; 534/16; 534/15; 534/14; 534/10; 424/9.263

(58) Field of Classification Search ........... 540/474, 540/465, 470, 455, 429; 424/9.263; 534/16, 534/10, 14, 15
See application file for complete search history.

(56) References Cited

U.S. PATENT DOCUMENTS

| 4,983,376 | A | * | 1/1991 | Sherry ................ 424/9.363 |
| 5,358,704 | A | * | 10/1994 | Desreux et al. ....... 424/9.363 |
| 5,428,155 | A | * | 6/1995 | Sherry et al. ............ 540/474 |
| 6,149,890 | A | * | 11/2000 | Uggeri et al. .......... 424/9.363 |

FOREIGN PATENT DOCUMENTS

WO   WO 95/31444   * 11/1995

OTHER PUBLICATIONS

Ranganathan et al., Polymethylated DOTA Ligands. 1. Synthesis of Rigidified Lanthanide Chelates and Studies on the Effect of Alkyl Substitution on Acid–Base Properties and Conformational Mobility, Inorganic Chemistry, vol. 41 No. 25, 2002, pp. 6846–6855.*
Ranganathan et al., Polymethylated DOTA Ligands. 2. Synthesis of Rigidified Lanthanide Chelates and Studies on the Effect of Alkyl Substitution Conformational Mobility and Relaxivity, Inorganic Chemistry, vol. 41 No. 25, 2002, pp. 6856–6866.*
Zoltan Kovacs and A. Dean Sherry, pH–Controlled Selective Protection of Polyaza Macrocycles, Synthesis, Jul. 1997, p. 761–763.
Shanrong Zhang, Patrick Winter, Kuangcong Wu and A. Dean Sherry, A Novel Europium (III)–Based MRI Contrast Agent, 2001 J. Am. Chem. Soc., pp. 1517–1518.
Shanrong Zhang, Kuangcong Wu, Michael C. Biewer and A. Dean Sherry, 1H and 17O NMR Detection of a Lanthanide-Bound Water Molecules at Ambient Temperatures in Pure Water as Solvent, Inorganic Chemistry, vol. 40, No. 17, 2001, p. 4284–4290.
Min K. Moi and Claude F. Meares, The Peptide Way to Macrocyclic Bifunctional Chelating Agents: Synthesis of 2-(p-Nitrobenzyl)-1, 4, 7, 10–tetraazacyclododecane–N,N', N", N"-tetraacetic Acid and Studyof its Yttrium(III) Complex, J. Am. Chem. Soc., 110, 1988, p. 6266–6267.
Mark Woods, Silvio Aime, Mauro Botta, Judith A. K. Howard, Janet M. Moloney, Michel Navet, David Parker, Marc Port, and Olivier Rousseaux, Correlation of Water Exhange Rate with Isomeric Composition in Diastereoisomeric Gadolinium Complexes of Tetra (carboxyethyl) dota and Related Macrocyclic Ligands, J. Am. Chem. Soc., vol. 122, No. 40, 2000, p. 9781–9792.
Rachel S. Dickens, Judith A. K. Howard, Christine L. Maupin, Janet M. Moloney, David Parker, Robert D. Peacock, James P. Riehl, and Giuliano Siligardi, Ground and Excited State Chiroptical Properties of Enantiopure Macrocyclic Tetran phthyl Lanthanide Complexes: Controlled Modulation of the Frequency and Polarisation of Emitted Light, New J. Chem., 1998, p. 891–899.
Ramachandran S. Ranganathan, Natarajan Raju, Helen Fan, Xun Zhang, Michael F. Tweedle, Jean F. Desreux, and Vincent Jacques, Polymethylated DOTA Ligands. 2. Synthesis of Rigidified Lanthanide Chelates and Studies on the Effect of Alkyl Substitution on Conformational Mobility and Relaxivity, Inorganic Chemistry, vol. 41, No. 25, 2002, p. 6856–6866.
Vinciane Comblin, Dominique Gilsoul, Martine Hermann, Valerie Humblet, Vincent Jacques, Mohammed Mesbahi, Christophe Sauvage, and Jean F. Desreux, Designing New MRI Contrast Agents: A Coordination Chemistry Challenge, Coordination Chemistry Reviews 185–186, 1999, p. 451–470.
Ranganathan; "Polymethylated Dota Ligands. 2. Synthesis of Rigidified Lanthanide Chelates And Studies on The Effect of Alkyl Substitution on Conformational Mobility And Relaxivity"; American Chemical Society Published on Web Nov. 15, 2002; pp. 6856–6866.
Comblin; "Designing new MRI contrast agents: a coordination chemistry challenge"; Coordination Chemistry Reviews (1999); pp. 451–470.

* cited by examiner

Primary Examiner—Johann Richter
Assistant Examiner—Chukwuma Nwaonicha

(57) ABSTRACT

The present invention is directed, in general, to a contrast agent comprising a tetraazacyclododecane ligand and comprising a macrocyclic ring and a paramagnetic metal ion coordinated to the tetraazacyclododecane ligand. Pendent arms R, R', R" and R'" attached to a ring nitrogen. The pendent arms have the general formula: $-C'HR^1R^2$ and for three or more of the pendent arms a chirality of the carbon atoms C' are identical for each of three or more of the pendent arms. The $R^1$ group is larger than hydrogen and $R^2$ is selected from the group consisting of: an alcohol, amides, a carboxylate, phosphinates and a phosphonate. One or more substituents $R^6$ is a group larger than a methyl group and is located on one or more ring carbons.

12 Claims, 5 Drawing Sheets

SELECTION OF COORDINATION GEOMETRY TO ADJUST WATER EXCHANGE RATES OF PARAMAGNETIC METAL ION-BASED MACROCYCLIC CONTRAST AGENTS

TECHNICAL FIELD OF THE INVENTION

The present invention is directed to the development of paramagnetic metal ion-based macrocyclic s contrast agents, and more particularly, to the selection of coordination geometries of the paramagnetic metal ion-macrocyclic complex to adjust the water exchange rate of the contrast agent.

BACKGROUND OF THE INVENTION

Contrast agents are widely used to enhance magnetic resonance imaging (MRI) contrast. The administration of traditional MRI contrast agents, such as gadolinium (Gd) chelated to DOTA (1,4,7,10-tetraazacyclododecane-1,4,7,10-tetraacetic acid), are thought to achieve contrast by the paramagnetic relaxation effect of a metal-ion to shorten the bulk water relaxation time via rapid exchange of the metal ion's inner-sphere water molecules with bulk solvent.

An alternative class of MRI contrast agents rely on chemical exchange saturation transfer (CEST) to enhance MRI contrast. For instance, the water exchange rates for water molecules bound to certain extrinsic paramagnetic metal ion-macrocyclic complexes incorporating the tetraazacyclododecane macrocyclic ring are sufficiently slow that a separate bound water magnetic resonance signal, substantially up-field or downfield (e.g., about ±6 ppm or more) from the bulk water magnetic resonance signal, is observable in pure water as solvent. This highly shifted and slowly exchanging bound water molecule may be irradiated to produce magnetization transfer (MT) on bulk water and thereby serve as an effective contrast agent.

For both traditional MRI and CEST contrast agents, the residence lifetime ($\tau_M$), is an important factor governing the effectiveness of a given contrast agent. The term $\tau_M$ as used herein refers to duration that inner-sphere water molecules associate with the paramagnetic metal ion-macrocyclic complexes. A water molecule that resides too long on the metal center of a traditional MRI contrast agent, for example, will occupy space that could otherwise be used to effect the paramagnetic relaxation of different water molecules, thereby reducing the overall effective paramagnetic relaxation of bulk water. On the other hand, if the water molecule does not reside on the paramagnetic metal ion-macrocyclic complexes for long enough, then effective paramagnetic relaxation also does not occur. It is generally believed therefore that traditional MRI contrast agents should optimally have a TM that is between about 10 and about 100 nanoseconds.

Contrary to the above-described traditional MRI contrast agents, it is desirable for CEST contrast agents to have a slow rate of water exchange. For example, some of the above-mentioned extrinsic paramagnetic metal ion-macrocyclic complexes have sufficiently slow water residence lifetimes (e.g., $\tau_M$ greater than about 1 microsecond) such that the highly shifted bound water magnetic resonance signal is observable at room temperature. This, in turn, facilitates the identification and irradiation of the highly shifted bound water magnetic resonance signal.

It has proven challenging, however, to design contrast agents having the tetraazacyclododecane ring structure incorporated therein so as to provide the desired $\tau_M$ value. At least part of the problem stems from the dynamic equilibrium that typically exists between different enantiomeric configurations of both the macrocyclic ring and the pendant arms coupled to the ring. The resident lifetime of a water molecule that is associated with the contrast agent can be substantially different for each of the enantiomeric configurations of the contrast agent. This, in turn, effects the suitability of the contrast agent for particular applications.

As an example, consider a contrast agent comprising a Gd(III)-DOTA complex. The macrocyclic ring of the Gd(III)-DOTA complex adopts a quadrangular (3333) conformation, with the torsion angle between the square defined by the nitrogen atoms, and a second square defined by coordinating oxygen atoms, defining the coordination geometry of the complex. A torsion angle of about 39° defines a capped square antiprismatic geometry, whereas a torsion angle of about 25° defines a capped twisted square antiprismatic geometry.

The conformation of each ethylene bridge in the macrocyclic ring is designated as λ or δ, according to the sign of the torsion angle. Thus, the conformation of the macrocyclic ring has either a (δδδδ) or (λλλλ) orientation. Similarly, a torsion angle between the carboxylic groups of the acetate pendant arm, the metal ion, and the ring nitrogen that the pendant arm is attached to, can have either a positive or negative sign, designated as Δ and Λ, respectively. Thus, the pendant arms can have either a Δ or Λ orientation.

Consequently, the Gd(III)-DOTA complex has four enantiomeric configurations that are in dynamic equilibrium with each other. The four stereoisomeric coordination geometries are summarized as: Δ(λλλλ), Λ(δδδδ), Δ(δδδδ) and Λ(λλλλ). When the orientations of the pendant arms and macrocyclic ring are identical (e.g., Δ(δδδδ), and Λ(λλλλ), then the Gd(III)-DOTA complex adopts the capped twisted square antiprismatic geometry. But when the orientations of the pendant arms and macrocyclic ring are opposite (e.g., Δ(λλλλ), and Λ(δδδδ), then the Gd(III)-DOTA complex adopts the capped square antiprismatic geometry.

It is generally believed that the measured $\tau_M$ value for the inner-sphere water molecules (about 244 nanoseconds) associated with the Gd(III)-DOTA complex is actually a weighted average of the resident lifetimes for each of these four stereoisomeric coordination geometries. The relatively long $\tau_M$ makes Gd-DOTA undesirable in the design of high relaxivity contrast media (e.g., a relaxivity at 298° C., $r_1^{298}$, of at least about 50 mM$^{-1}$s$^{-1}$) Moreover, it has been suggested that the resident lifetime of inner-sphere water molecules associated with the Gd(III)-DOTA complex is substantially different (e.g., about one or two orders of magnitude) for the two geometries.

Accordingly, what is needed is a contrast agent whose stereoisomeric coordination geometries can be selected among the available isomers, and thereby have the desired $\tau_M$ value for particular magnetic resonance imaging applications, thus avoiding problems encountered with previous contrast agents.

SUMMARY OF THE INVENTION

To address the deficiencies of the prior art, the present invention, in one embodiment, provides a contrast agent comprising a paramagnetic metal ion coordinated to a tetraazacyclododecane ligand, the tetraazacyclododecane ligand having the following general structural formula:

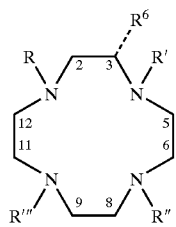

The tetraazacyclododecane ligand comprises a macrocyclic ring and pendant arms, R, R', R" and R'", attached to a ring nitrogen. The pendant arms have the general formula: —C'HR$^1$R$^2$. For three or more of the pendant arms, a chirality of the carbon atoms C' are identical to each other. R$^1$ are groups larger than hydrogen. R$^2$ can be an alcohol (—CH$_2$OH), an amide (—CONR$^3$R$^4$, where R$^3$ and R$^4$ are organic groups), a carboxylate (—COOH), a phosphinates (—PO$_2$HR$^5$, where R$^5$ is an organic group), or a phosphonate (—PO(OH)$_2$). One or more of substituents R$^6$ is a group larger than a methyl group and is located on one or more ring carbons.

In another embodiment, the present invention provides a method of using a magnetic resonance contrast agent. The method comprises subjecting a sample containing the contrast agent to a radio frequency pulse. The contrast agent is a tetraazacyclododecane ligand having a general formula of:

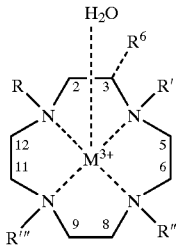

and comprising a macrocyclic ring, pendant arms R, R', R" and R'" and one or more of substituents R$^6$, as described above. The tetraazacyclododecane ligand further includes a paramagnetic metal ion (M$^{3+}$) coordinated to said tetraazacyclododecane ligand and a water molecule (H$_2$O) associated with the tetraazacyclododecane ligand. The method further includes obtaining a magnetic resonance signal by applying a radio frequency pulse at about a resonance frequency of water.

Yet another embodiment provides a magnetic resonance system, comprising the above-described tetraazacyclododecane ligand that further includes a paramagnetic metal ion (M$^{3+}$) coordinated to the tetraazacyclododecane ligand and a water molecule (H$_2$O) associated with the tetraazacyclododecane ligand. The system further includes a magnetic resonance apparatus configured to produce a radio-frequency pulse and the magnetic resonance contrast agent produces a magnetic resonance signal when subjected to the radio-frequency pulse.

The foregoing has outlined, preferred and alternative features of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention. Those skilled in the art should also realize that such equivalent constructions do not depart from the scope of the invention.

BRIEF DESCRIPTION OF THE DRAWINGS

For a more complete understanding of the invention, reference is now made to the following descriptions taken in conjunction with the accompanying drawing, in which.

DETAILED DESCRIPTION

Figure 1:
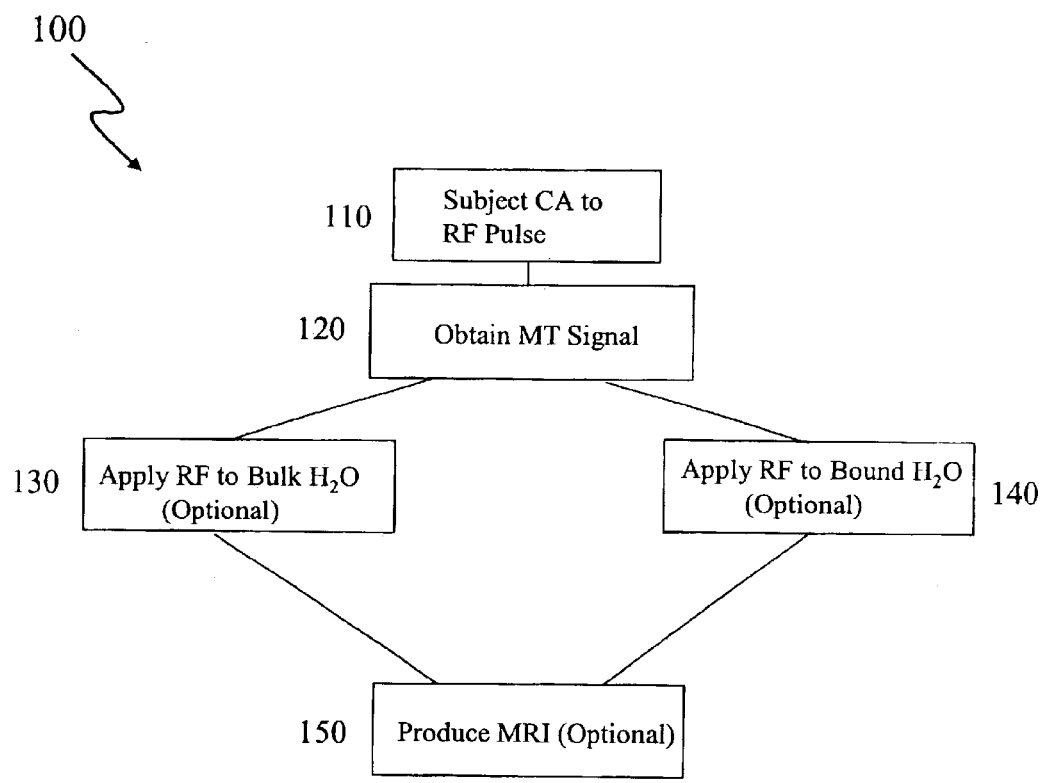
FIG. 1 illustrates a method of using a magnetic resonance contrast agent according to the present invention.

The present invention recognizes that certain paramagnetic metal ion-macrocyclic complexes having a tetraazacyclododecane macrocyclic ring, with substituents and pendant arms coupled thereto, are locked into a particular desired coordination geometry. This is achieved by both coupling suitable substitutes to carbon atoms of the macrocyclic ring, and the use of particular pendant arm structures attached to the ring nitrogen atoms, as further explained below. Such paramagnetic metal ion-macrocyclic complexes provide inner-sphere water molecules associated with the complex having different resident lifetimes than heretofore obtainable. Consequently, the present invention allows magnetic resonance contrast agents to be designed to provide either a fast or slow water exchange, as desired, for either traditional MRI or CEST contrast agents.

The term lock, as used herein, means that the conformational ring flipping motion of the macrocyclic ring and pendant arm rotation are inhibited such that either a capped twisted square antiprismatic or a capped square antiprismatic geometry. The interconversions of the macrocyclic ring orientations (δδδδ) or (λλλλ) and pendant arm orientations Δ or Λ, can be observed by nuclear magnetic resonance exchange spectroscopy (EXSY), as illustrated in the example section below.

One embodiment of the present invention is a magnetic resonance contrast agent. The contrast agent comprises a paramagnetic metal ion coordinated to a tetraazacyclododecane ligand, the tetraazacyclododecane ligand having the following general structural formula:

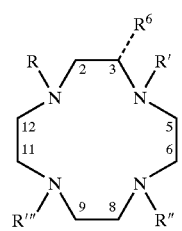

The tetraazacyclododecane ligand comprises a macrocyclic ring and pendant arms, R, R', R" and R'", attached to a ring nitrogen. The pendant arms have the general formula:

—C'HR$^1$R$^2$. For three or more of the pendant arms, a chirality of the carbon atoms C' are identical to each other. R$^1$ are groups larger than hydrogen. R$^2$ can be an alcohol (—CH$_2$OH), an amide (—CONR$^3$R$^4$, where R$^3$ and R$^4$ are organic groups), a carboxylate (—COOH), a phosphinates (—PO$_2$HR$^5$, where R$^5$ is an organic group), or a phosphonate, (—PO(OH)$_2$). One or more of substituents R$^6$ is a group larger than a methyl group and is located on one or more ring carbons.

In embodiments where only three pendent arms have the above described characteristics, the fourth pendent arm can be any organic groups. For instance, the fourth pendent arm can be a hydrogen or larger group that is achiral, or has the opposite chirality as the carbon atom C' of the other three pendent arms. In addition, one skilled in the art would understand that in order for the carbon atom C' of the three or more of the pendant arms to be chiral, the R$^1$ and R$^2$ substituents are different from each other. Also, the chemical composition of R$^1$ and R$^2$ need not be the same on each of the three or more pendent arms. For example, in some embodiments, R$^1$ is an alkyl group, such as a methyl group, and R$^2$ is a carboxylate group (-COOH) group. In other embodiments, R$^1$ is an aromatic group, such as a benzyl, and R$^2$ is an alcohol group (—CH$_2$OH). In other embodiments, however, for one of the three or more pendant arms, R$^1$ is an alkyl group and R$^2$ is an alcohol group, while for the other two pendant arms R$^1$ is a different alkyl group or an aromatic group and R$^2$ is an alcohol group or a carboxylate group.

Moreover, each of the ring carbons having a R$^6$ substituent that is larger than a methyl group can have different chemical compositions than each other. The R$^6$ substituents larger than a methyl group can be located on any one or more ring carbons 2, 3, 5, 6, 8, 9, 11 and 12. The number of R$^6$ substituents and their chemical compositions are selected to provide sufficient conformational hinderance to lock the macrocyclic ring of the tetraazacyclododecane ligand into a particular coordination geometry.

In general, if the substituents R$^6$ are large, then a lesser number of ring carbons need to be substituted in order to lock the tetraazacyclododecane ligand into a particular coordination geometry. In some embodiments, for example, a substituent on ring carbon 2 is a nitrobenzyl group, such as para-nitrobenzyl, and the remaining ring carbons are substituted with hydrogen. In other embodiments, ring carbons 2, 5, 8 and 11 are substituted with hydroxypropyl groups, such as —CH$_2$—CH$_2$—CH$_2$OH, and the remaining ring carbons are substituted with hydrogen.

The chirality of the three or more pendant arm carbon atoms C' and the one or more R$^6$-substituted ring carbons is selected so as to lock the tetraazacyclododecane ligand into one of a capped square antiprism or a capped twisted square antiprism configuration. A capped twisted square antiprism configuration is defined when the three or more pendant arm carbon atoms C' and the macrocyclic ring have the same orientations. Alternatively, a capped square antiprism configuration is defined when the three or more pendant arm carbon atoms C' have the opposite orientations as the macrocyclic ring.

For example, when the three or more pendant arm carbon atoms C' have Δ orientations and the chirality of the one or more R$^6$-substituted ring carbons is selected such that the macrocyclic ring has an identical (δδδδ) orientation, then the tetraazacyclododecane ligand has a capped twisted square antiprism configuration. Or, when the three or more pendant arm carbon atoms C' have Λ orientations arid the chirality of the one or more ring carbons is selected such that the macrocyclic ring has a (λλλλ) orientation, then the tetraazacyclododecane ligand again has a capped twisted square antiprism configuration.

Alternatively, when the three or more pendant arm carbon atoms C' have Δ orientations and the chirality of the one or more ring carbons is selected such that the macrocyclic ring has an opposite (λλλλ) orientation, then the tetraazacyclododecane ligand has a capped square antiprism configuration. Or, when the three or more pendant arm carbon atoms C' have Δ orientations and the chirality of the one or more ring carbons is selected such that the macrocyclic ring has a (δδδδ) orientation, then the tetraazacyclododecane ligand again has a capped square antiprism configuration.

As noted above, the particular configuration that the tetraazacyclododecane ligand is locked into effects the $\tau_M$ of a water molecule associated with the contrast agent. For instance, a tetraazacyclododecane ligand that is locked into a capped twisted square antiprism configuration will have a faster exchange rate than an analogous tetraazacyclododecane ligand that is locked into a capped square antiprism configuration. Moreover, the exchange rate or residence time of the water molecule associated with the contrast agent can be further adjusted through the selection of particular R$^2$ groups. A bulky R$^2$ group tend to push the bound water molecule away from the metal ion, increasing the rate of water exchange. A charged R$^2$ group increases the electronic deficiency of the metal ion, thereby making the water molecule more strongly bound, decreasing the rate of water exchange.

For instance, in certain preferred embodiments of the contrast agent, the tetraazacyclododecane ligand has a capped twisted square antiprism coordination geometry and the R$^2$ group is the alcohol or amide. Because R$^2$ has a neutral charge and is not a bulky group, it provides relatively weak hindrance to access of the water molecule to the metal ion. Consequently, the resident lifetime of a water molecule associated with the tetraazacyclododecane ligand and the paramagnetic metal ion is long. For instance, in certain embodiments, the residence lifetime at about 298°K, $\tau_M^{298}$, is between about 1 and about 100 microseconds. Such embodiments are preferably used as CEST contrast agents, for example.

In other embodiments of the contrast agent where the tetraazacyclododecane ligand has a capped twisted square antiprism coordination geometry, the R$^2$ group is the carboxylate group. Because the R$^2$ group is charged it provides a relatively less electron deficient metal ion. Therefore a water molecule associated with the tetraazacyclododecane ligand and the paramagnetic metal ion has a shorter residence lifetime. For example, in some embodiments at about 298°K, $\tau_M^{298}$ is between about 10 and about 100 nanoseconds. Such embodiments are preferably used as traditional MRI contrast agents, fore example.

In yet other embodiments of the contrast agent the tetraazacyclododecane ligand has a capped square antiprism coordination geometry. In some embodiments, if the R$^2$ group is the alcohol or amide group, then a water molecule associated with the tetraazacyclododecane ligand and the paramagnetic metal ion has a residence lifetime at about 298°K, $\tau_M^{298}$, of between about 10 and about 5000 microseconds. In similar embodiments having a capped square antiprism coordination geometry, if the R$^2$ group is the carboxylate, then the water molecule has a residence lifetime at about 298°K, $\tau_M^{298}$, of between about 100 and about 500 nanoseconds. Alternatively, if the R$^2$ group is the phosphonate or phosphinate, then the bulkiness of the R$^2$ group will provide a relatively strong hindrance to access of the water molecule to the metal ion. In some such embodiments, the water molecule has a residence lifetime at about 298°K, $\tau_M^{298}$, of between about 10 and about 100 nanoseconds.

The selection of the $R^6$-substituted ring carbons to provide a particular pendent arm orientation depends upon the desired priority of the groups associated with these chiral centers. One skilled in the art would understand how the Cahn-Ingold-Prelog priority rules are applied to determine whether a particular chiral center is an R or S enantiomer. For instance, consider embodiments of the contrast agent where the priority of the $R^6$-substituted ring carbon is lower than the priority of the ring carbon and nitrogen that it is bonded to. In this case, if the configuration of the one or more $R^6$-substituted ring carbons is S, then the conformation of the macrocyclic ring will be locked into a (δδδδ) orientation.

If, however, the configuration of the one or more $R^6$-substituted ring carbons is R, then the conformation of the macrocyclic ring will be locked into a (λλλλ) orientation. In alternative embodiments of the contrast agent, the priority of the $R^6$-substituted ring carbon is higher than the priority of the ring carbon and nitrogen that it is bonded to. In such embodiments, a configuration the one or more $R^6$-substituted ring carbons being S and R locks the macrocyclic ring into (λλλλ) and (δδδδ) orientations, respectively.

Similar considerations apply to selecting the chirality of the three or more pendant arm C' carbon atoms. For instance, in some embodiments, the priority of the $R^1$ group is lower than the priority of the ring nitrogen and $R^2$ group that it is bonded to. In such embodiments, the configuration of the C' carbon atoms is R, which, in turn, locks the three or more pendant arms into a Λ orientation. If, however, the configuration of the C' carbon atoms is S, then the three or more pendant arms are locked into a Δ orientation. In other embodiments, the priority of the $R^1$ group is higher than the priority of the ring nitrogen and $R^2$ group that it is bonded to. In these embodiments, C' carbon atom configurations of S or R lock the three or more pendant arms into Λ or Δ orientations, respectively.

As a further example, and as illustrated in the example section below, one exemplary contrast agent of the present invention is Gd(III) (2S) 2-p-nitrobenzyl- (1S, 4S, 7S, 10S)-α, α', α", α'"-tetramethyl-1,4,7,10-tetrazacyclododecane-1,4,7,10 tetraacetic acid (abbreviated as S-SSSS-NO₂BnDOTMA), with a $\tau_M$ of about 15 nanoseconds. Gd-coordinated S-SSSS-NO₂BnDOTMA corresponds to a contrast agent where $R^1$ and $R^2$ on each of the pendant arms R, R', R" and R'" are methyl and carboxylate (—COOH) groups, respectively and the chirality of pendant arms carbon atoms C' are all S, ring carbon 2 is substituted with $R^6$ group comprising a para-nitrobenzyl group, with ring carbon 2 having a chirality of S, and with the other ring carbon substituted with hydrogen atoms.

In certain preferred embodiments of the contrast agent, it is desirable for at least one of the $R^6$ substituents that is larger than a methyl group to further include a functional group. The functional group is selected so as to facilitate the attachment of the tetraazacyclododecane ligand to a carrier component, such as a biomolecule, dedrimer, polypeptide, etc . . . , using procedures well known to those skilled in the art. Examples of suitable functional groups attached to $R^6$ include amino groups, carboxylate, isothiocyanates or maleiimdes. One example of such a functionalized $R^6$ substituent is a (para-isothiocyantobenzyl) group.

The use of any paramagnetic metal ion in the contrast agent is within the scope of the invention. In certain preferred embodiments of the contrast agent, the paramagnetic metal ion coordinated to the tetraazacyclododecane ligand is a lanthanide ion. The choice of a particular lanthanide depends on the type of contrast agent desired. For instance, lanthanide ions having a large magnetic moment, such as Gd(III) Dy(III) or Ho(III), are preferred in traditional MRI contrast agents. For CEST contrast agents, at magnetic field strengths below 4.7 Tesla, some of the preferred lanthanide ions include Eu(III), Tb, (III) Dy(III) or Ho(III). At higher field strengths, some preferred lanthanide ions include Pr(III), Nd(III), Sm(III), Er(III) or Tm(III).

Another embodiment of the present invention is a method 100 of using a magnetic resonance contrast agent. As illustrated in FIG. 1, the method 100 comprises subjecting a contrast agent contained within a sample to a radio-frequency (RF) pulse, in step 110. Here, the contrast agent (CA) is a tetraazacyclododecane ligand having the general formula as presented below:

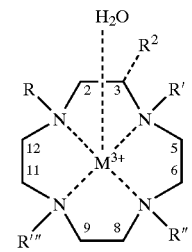

The tetraazacyclododecane ligand can comprise any of the above-described embodiments of the macrocyclic ring having substituents $R^6$ and pendant arms, R, R', R" and R'", attached to a ring nitrogen. The tetraazacyclododecane ligand further includes a paramagnetic metal ion ($M^{3+}$) coordinated to the tetraazacyclododecane ligand and a water molecule ($H_2O$) associated with the tetraazacyclododecane ligand.

The method 100 further comprises obtaining, in step 120, a magnetic resonance (MR) signal is obtained by applying a radio-frequency pulse at about a resonance frequency of water. In certain embodiments of the method 100, the magnetic resonance signal is obtained by applying, in step 130, the radio-frequency pulse at about a resonance frequency of bulk water (i.e., water not associated with the tetraazacyclododecane ligand) as part of a conventional magnetic resonance protocol to generate spin-lattice (T1) or spin-spin (T2) weighted signals, for example. In other embodiments, the magnetic resonance signal is obtained by applying, in step 140, the radio-frequency pulse as a saturating pulse at a resonance frequency of the water molecule ($H_2O$) associated with tetraazacyclododecane ligand, as part of CEST protocol to generate magnetization transfer signals. Optionally, method 100 may further include producing an MRI, in step 150. Those skilled in the art understand that other conventional means of producing magnetic resonance signals and images, are within the scope of the present invention.

In certain preferred embodiments of the method 100, the contrast agent further includes a carrier component, conjugated to one or more of the functionalized substituents $R^6$, as discussed above. In certain embodiments of the present invention, the CA includes at least one and up to twenty of the tetraazacyclododecane ligands. Such ligands may be covalently or noncovalently bonded to a carrier component, such as described above, comprising a portion of the contrast agent. Collecting several such ligands, and associated metal ions and bound water molecules, allows a larger effective magnetic resonance signal to be achieved at lower concentrations of contrast agent. In certain such embodiments, where the water molecule ($H_2O$) associated with the tetraazacyclododecane ligand has a $\tau_M^{298}$, of between about 10 and about 100 nanoseconds, the water molecule associated with a contrast agent that further includes a carrier component has a relativity at 298° C., $r_1^{298}$, of at least about 50 $mM^{-1}s^{-1}$.

Figure 2:
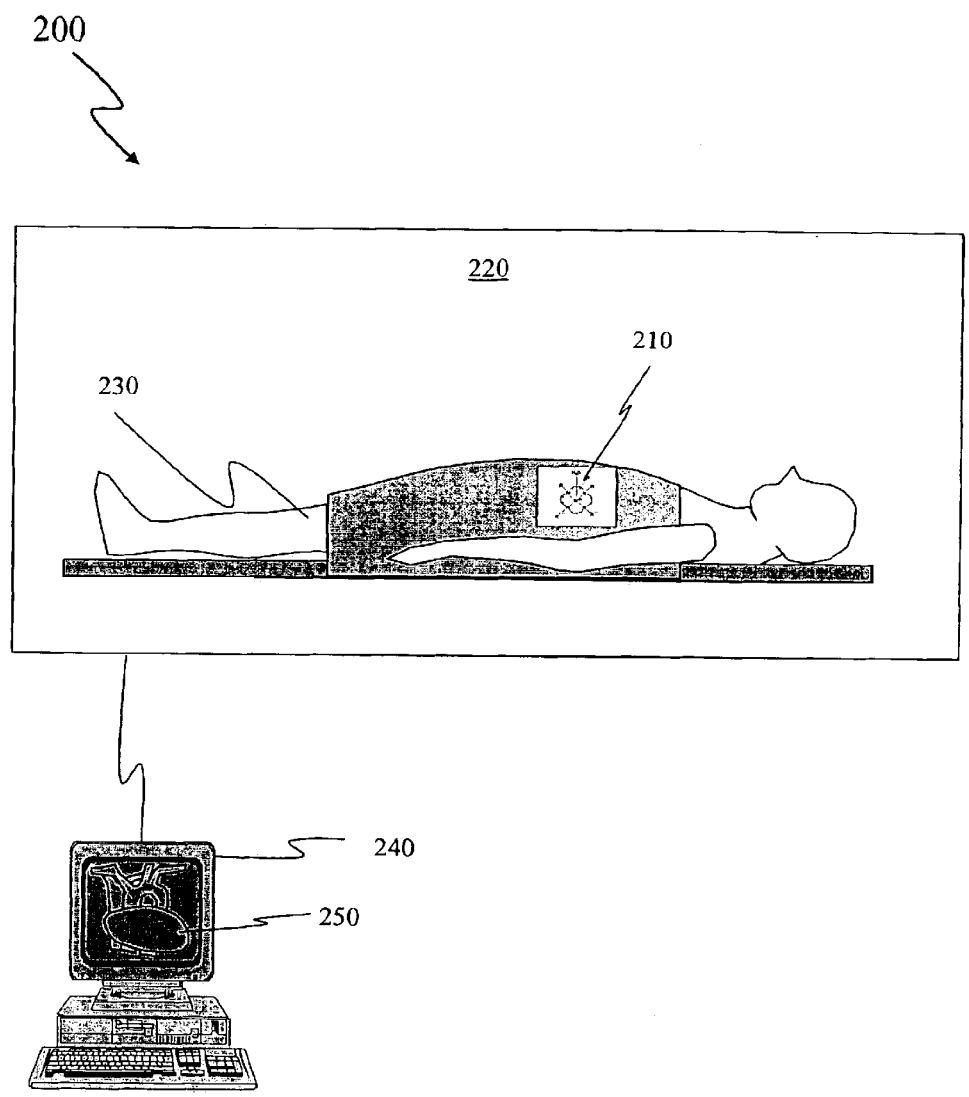
FIG. 2 illustrates a magnetic resonance system according to the present invention.

Yet another embodiment of the present invention is a magnetic resonance system 200. As illustrated in FIG. 2, the system 200 comprises a magnetic resonance contrast agent 210. The contrast agent contains a tetraazacyclododecane ligand of the same general formula and various embodiments, as described for method 100 and elsewhere herein. The contrast agent 210 further includes a paramagnetic metal ion coordinated to a water molecule, referred to as a bound water molecule (bound $H_2O$) and associated with the tetraazacyclododecane ligand.

The system 200 further comprises a magnetic resonance apparatus 220. One of ordinary skill in the art understands that the magnetic resonance apparatus may include all the hardware and software components necessary to produce magnetic resonance spectra or images from the magnetic resonance signal in the presence of the contrast agent, as described above.

The system 200 may further comprise a sample 230 that contains the CA 220 within it. The sample 230 includes living subjects, including animals, such as humans, or a portion of fluid or tissue withdrawn from the living subject. Alternatively, the sample 230 containing the contrast agent 220 may be an inanimate object, or contain other non-living material. In one preferred embodiment of the magnetic resonance system 200, the magnetic resonance apparatus 210 includes a computer 240 capable of producing a magnetic resonance image 250 of at least a portion of the sample 230 from the magnetic resonance signal.

Having described the present invention, it is believed that the same will become even more apparent by reference to the following examples. It will be appreciated that the examples are presented solely for the purpose of illustration and should not be construed as limiting the invention. For example, although the experiments described below may be carried out in laboratory or pilot plant setting, one skilled in the art could adjust specific numbers, dimensions and quantities up to appropriate values for a full scale plant.

EXAMPLES

Examples of contrast agents of the present invention are presented below for illustrative purposes and do not limit the scope of the claimed invention. The synthesis of polyazamacrocyles having pendent arms comprising organic substitutants has been described in: U.S. Pat. No. 5,428,155, to Sherry A. D. and van Westrenen, J.; Kovacs and Sherry, *pH-Controlled Selective Protection of Polyaza Macrocycles,* SYNTHESIS, 761–63, (July 1997) ("Kovacs and Sherry"); Zhang S., Winter P., Wu. K. & Sherry A. D., *A Novel Europium(III)-Based Contrast Agent,* 123 J. AM. CHEM. SOC. 1517–18 (2001); Zhang S., Wu. K., Biewer M. C., & Sherry A. D. $^1H$ and $^{17}O$ *NMR Detection of a Lanthanide-Bound Water Molecule at Ambient Temperatures in Pure Water,* 40 INORG. CHEM. 4284–90 (2001); all of which are incorporated herein by reference. The preparation of S-2-(nitrobenzyl)-1,4,7,10-tetraazacyclododecane has been described in Moi, Min K., Meares, C. F.; DeNardo, S. J., The peptide way to macrocyclic bifunctional chelating agents: synthesis of 2-(p-nitrobenzyl)-1,4,7,10-tetraazacyclododecane-N,N',N'',N'''-tetraacetic acid and study of its yttrium(III) complex, 110(18) J. AM. CHEM. SOC. 6266–7 (1988), and the alkylation of tetraazacyclododecane with Hünig's base has been described in Kovacs and Sherry, cited above, both of which are incorporated herein by reference.

Two stereoisomers of a contrast agent were synthesized: (2S) 2-p-nitrobenzyl-(1S, 4S, 7S, 10S)-α, α', α'', α'''-tetramethyl-1,4,7,10-tetraazacyclododecane-1,4,7,10 tetraacetic acid (abbreviated as S-SSSS-NO$_2$BnDOTMA) and (2S) 2-p-nitrobenzyl-(1R, 4R, 7R, 10R)-α, α', α'', α'''-tetramethyl-1,4,7,10-tetraazacyclododecane-1,4,7,10 tetraacetic acid (abbreviated as S-RRRR-NO$_2$BnDOTMA), as depicted below:

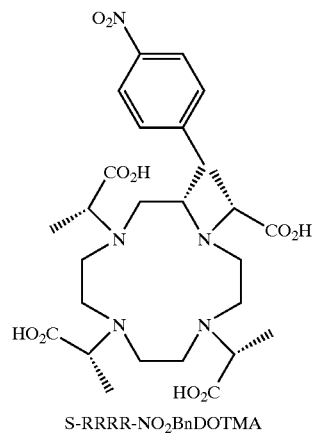

S-RRRR-NO$_2$BnDOTMA

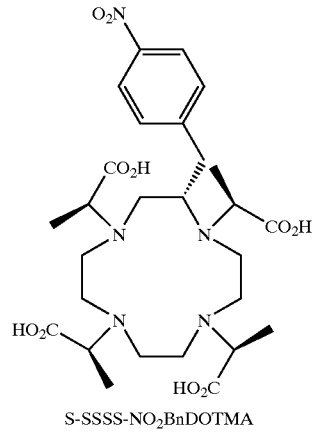

S-SSSS-NO$_2$BnDOTMA

S-2-(Nitrobenzyl)-1,4,7,10-tetraazacyclododecane was alkylated using either D or L ethyl O-trifluoromethansulfonyl lactate in chloroform with Hünig's base to afford the tetraethyl esters of the isomers of 2-(nitrobenzyl)-DOTMA. After purification by column chromatography (SiO$_2$, 20% THF in chloroform) the esters were hydrolyzed using lithium hydroxide in THF and water, followed by acidification with hydrochloric acid. The isolated ligands S-RRRR-NO$_2$BnDOTMA and S-SSSS-NO$_2$BnDOTMA were then used to form the paramagnetic metal ion complexes using the appropriate lanthanide chloride (pH 5.5, 60 ° C., 48 h). The complexes so obtained were then purified by reverse-phase (C-18) semi-preparative High Performance Liquid Chromatography.

Figure 3A:
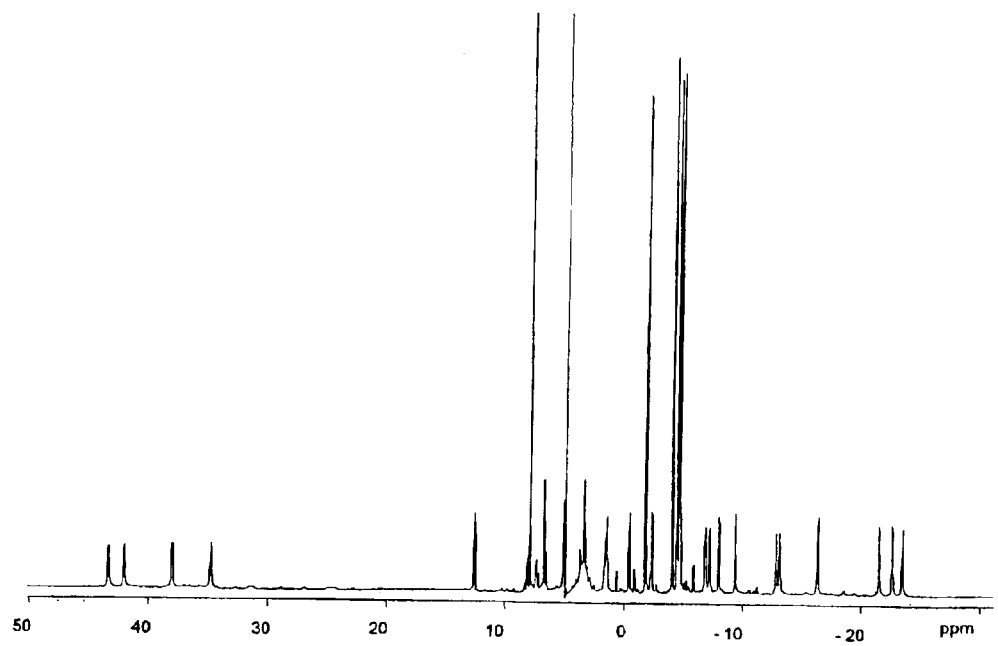
FIG. 3A and FIG. 3B illustrates exemplary $^1$H NMR spectra of [Eu(S-RRRR-NO$_2$BnDOMA)]$^-$ and [Eu(S-SSSS-NO$_2$BnDOTMA)]$^-$, respectively, produced according to the present.
Figure 3B:
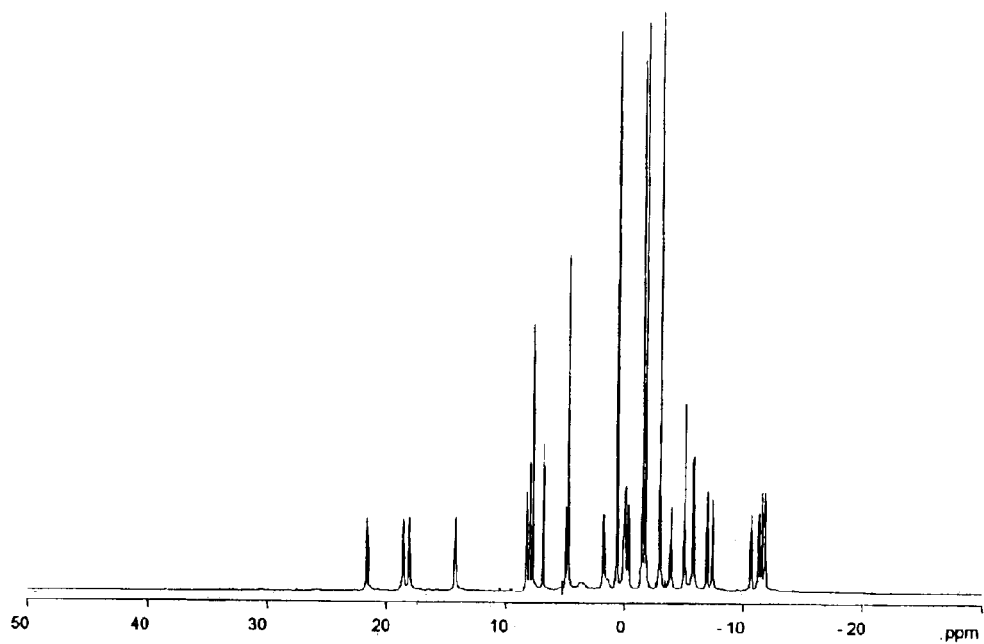

FIGS. 3A and 3B shows exemplary extended sweep width high resolution $^1H$ NMR spectra of [Eu(S-RRRR- $NO_2BnDOTMA)]^-$ (FIG. 3A) and [Eu(S-SSSS-$NO_2BnDOTMA$)]⁻ (FIG. 3B), recorded at 270 MHz in $D_2O$ at pH 5 (the * in the FIGURE denotes the HOD peak). The $^1H$ NMR spectra clearly reveals the presence of only one isomeric coordination geometry in each of the prepared complexes. $^1H$ NMR signals corresponding to the axial proton resonances at between about 35 and about 45 ppm for the [Eu(S-RRRR-$NO_2BnDOTMA$)]⁻ isomer, shown in FIG. 3A, are consistent with the expected square antiprismatic geometry ($\Delta(\lambda\lambda\lambda\lambda)$). $^1H$ NMR signals corresponding to the axial proton resonances at between about 15 and about 25 ppm for the [Eu(S-SSSS-$NO_2BnDOTMA$)]⁻ isomer, shown in FIG. 3B, are consistent with the expected the more open twisted square antiprismatic geometry ($\Delta(\delta\delta\delta\delta)$).

Selected physical-chemical differences between the two isomers were also investigated. For instance, the hydration states of the europium complexes of these two isomers was measured using Horrock's method described in W. D. Horrocks, Jr., D. R. Sudnick, 101 J. AM. CHEM. SOC. 334 (1979), and Parker's revised method described in A. Beeby, et al. 2 J. CHEM. SOC., PERKIN TRANS. 493 (1999), all of which are incorporated by reference herein. The hydration states of [Eu(S-RRRR-$NO_2BnDOTMA$)]⁻ and [Eu(S-SSSS-$NO_2BnDOTMA$)]⁻ were determined to have one inner sphere water molecule coordinated to each complex, as expected. The values of the hydration states (q) given by Horrock's method, and the revised method ($q_{corr}$) of Parker are summarized in Table 1.

TABLE 1

| | [Eu (S-RRRR-$NO_2BnDOTMA$) ]⁻ | [Eu (S-SSSS-$NO_2BnDOTMA$) ]⁻ |
|---|---|---|
| q | ~1.16 | ~0.98 |
| $q'_{corr}$ | ~1.00 | ~0.81 |

Regardless of the method employed, the hydration state of the isomer having a twisted square antiprismatic geometry [Eu(S-SSSS-$NO_2BnDOTMA$)]⁻ has about 0.16 smaller water molecules than that obtained for the [Eu(S-RRRR-$NO_2BnDOTMA$)]⁻ isomer having a square antiprismatic geometry. Based on the well-known strong distance dependence of the quenching effects of OH oscillators, this observation is consistent with a longer $Eu^{3+}$-water bond distance for [Eu(S-SSSS- $NO_2BnDOTMA$)]⁻, the twisted square antiprismatic geometry.

Figure 4:
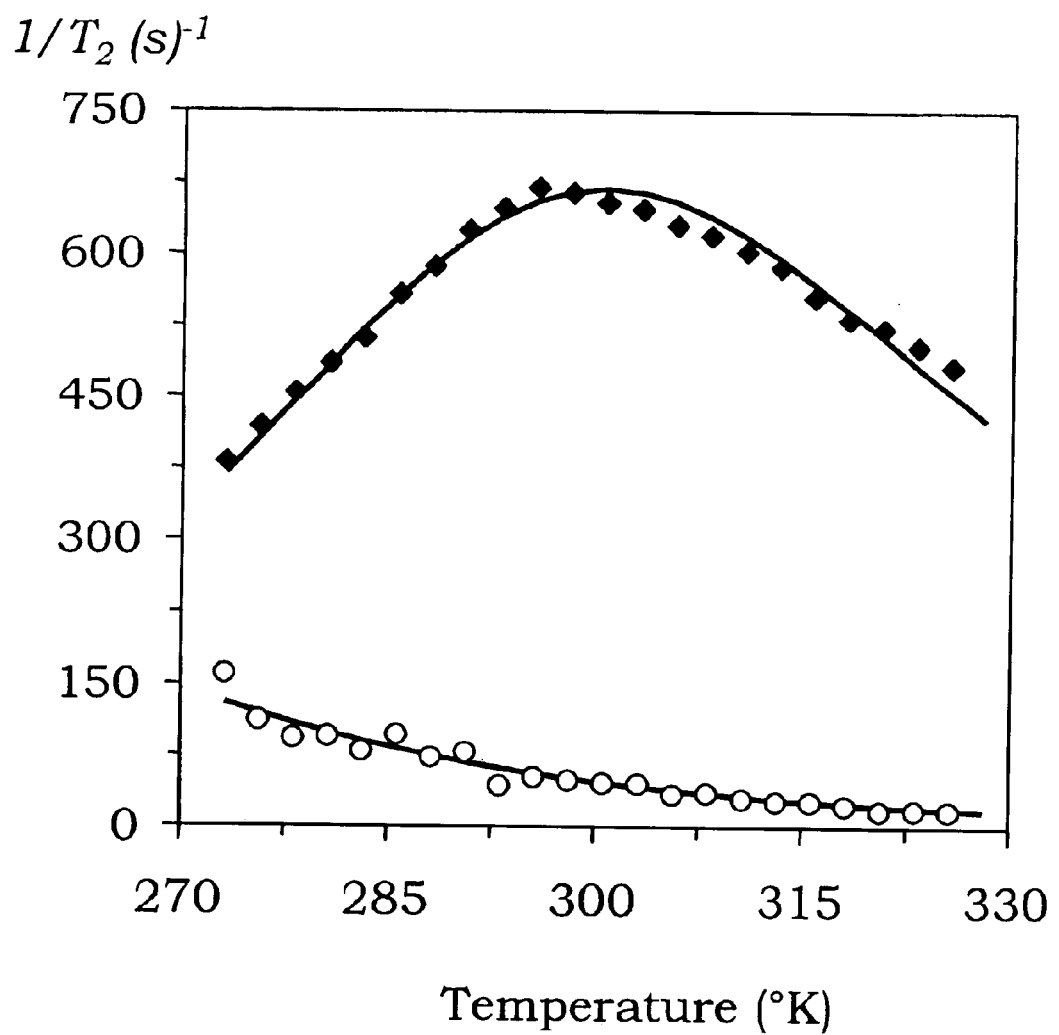
FIG. 4 presents a exemplary data showing the relationship between transverse relaxation rate (T$_2$) and temperature of [Gd(S-RRRR-NO$_2$BnDOTMA)]$^-$ (diamonds) and [Gd(S-SSSS-NO$_2$BnDOTMA)]$^-$ (circles).

The water exchange rates for [Gd(S-RRRR-$NO_2BnDOTMA$)]⁻ and [Gd(S-SSSS-$NO_2BnDOTMA$)]⁻ were also measured. As well known by those skilled in the art, the rate of water exchange is reflected in the transverse relaxation rate ($T_2$) of $^{17}O$ nuclei in the bulk solvent. Thus, water exchange rates are obtained by line-width analysis of the $^{17}O$ NMR spectra of the solvent recorded as a function of temperature. FIG. 4 shows exemplary transverse relaxation rates ($1/T_2$) of [Gd(S-RRRR-$NO_2BnDOTMA$)]⁻ (diamonds) and [Gd(S-SSSS-$NO_2BnDOTMA$)]⁻ (circles) as a function of temperature, determined at 11.25 Tesla.

The two complexes [Gd(S-RRRR- $NO_2BnDOTMA$)]⁻ and [Gd(s-ssss- N)$_2BnDOTMA$)]⁻ have substantially different $1/T_2$-temperature profiles, indicating substantially different water exchange rates. The profile for [Gd(S-RRRR-N)$_2BnDOTMA$)]⁻, rises, maximizes and then falls away with increasing temperature, indicative of fairly slow water exchange. In contrast, the profile for [Gd(S-SSSS-$NO_2BnDOTMA$)]⁻, did not reach a maximum within the temperature range study, indicative of a more rapid water exchange. The values of $\tau_M^{298}$ obtained by fitting procedures, well known to those skilled in the art, to profiles such as depicted in FIG. 4, are summarized in TABLE 2. Also shown in TABLE 2 are the relaxivities of water molecules associated with these isomers at 25 and 37° C.

TABLE 2

| | | [Gd (S-RRRR-$NO_2BnDOTMA$) ]⁻ | [Gd (S-SSSS-$NO_2BnDOTMA$) ]⁻ |
|---|---|---|---|
| $r_1^{298}$ | (mM⁻¹s⁻¹) | ~4.96 | ~5.20 |
| $r_1^{310}$ | (mM⁻¹s⁻¹) | ~3.84 | ~3.84 |
| $\tau_M^{298}$ | (nanoseconds) | ~120 | ~15 |

The $\tau_M$ obtained for the twisted square antiprismatic isomer [Gd(S-SSSS-$NO_2BnDOTMA$)]⁻ is about one order of magnitude shorter than that of the square antiprismatic [Gd(S-RRRR-$NO_2BnDOTMA$)]⁻. Such a large difference in water exchange rates clearly renders the more quickly exchanging isomer preferable for use in the design of high relaxivity magnetic resonance contrast agents.

The effect of these differing water exchange rates upon the relaxivity of [Gd(S-RRRR-$NO_2BnDOTMA$)]⁻ and [Gd(S-SSSS-$N0_2BnDOTMA$)]$^{31}$ is small, however. For such low molecular weight contrast agents, the water relaxivity at the magnetic resonance frequency used in the present experiments is strongly influenced by the rotational reorientation of the complex ($\tau_R$) Since the two complexes are isomeric, they are expected to exhibit about the same $\tau_R$ values and hence the relaxivity is limited to a similar extent in each case, regardless of water exchange rate. Thus, even though [Gd(S-SSSS-$NO_2BnDOTMA$)]⁻ has an about one order of magnitude faster water exchange rate than [Gd(S-SSSS-$NO_2BnDOTMA$)]⁻, the former isomer's relaxivity is only about 5 percent higher than the later isomer at 25° C., and about the same at 37° C. The benefits of faster water exchange rate are expected to become more evident for more slowing rotating contrast agents, having a longer $\tau_R$. For instance, in embodiments where [Gd(S-SSSS-$NO_2BnDOTMA$)]⁻ is coupled to a carrier component, such as a protein, with a slowly rotating structure, a $r_1^{298}$ of greater than about 50 mM⁻¹s⁻¹), is predicted.

Although the present invention has been described in detail, those skilled in the art should understand that they can make various changes, substitutions and alterations herein without departing from the scope of the invention.

What is claimed is:

1. A magnetic resonance contrast agent compound comprising: a tetraacyclododecane ligand having a general structural formula as follows:

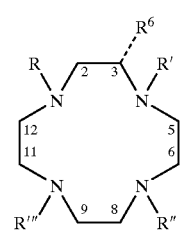

and comprising a macrocylic ring and wherein pendant arms R, R', R" and R'" attached to a ring nitrogen have the general formula: —C'HR$^1$R$^2$ and for three or more of said pendant arms a chirality of said carbon atoms C' are identical for each of said three or more pendant arms, said R' are groups larger than hydrogen, and said R$^2$ is selected from the goup consisting of:

an alcohol (—CH$_2$OH);

amides (—CONR$^3$R$^4$, where R$^3$ and R$^4$ are organic groups);

a carboxyl(—COOH);

phosphinates (—PO$_2$HR$^5$, where R$^5$ is an organic group); and a phosphonate (—PO(OH)$_2$); and wherein one or more of substituents R$^6$ is a group larger than a methyl group and is located on one or more ring carbons; and a paramagetic metal ion coordinated to said tetraazacyclododecane ligand.

2. The magnetic resonance contrast agent compound as recited in claim 1, wherein said chirality of said carbon atoms C' provides said three or more of said pendant arms with a Λ or Δorientation, and wherein a chirality of a ring carbon bonded to said one or more of substituents R$^6$ provides said macrocyclic ring with an identical orientation, λλλλ or δδδδ, respectively, said tetraazacyclododecane ligand thereby having a monocapped twisted square antiprism coordination geometry.

3. The magnetic resonance contrast agent compound as recited in claim 2, wherein said R$^2$ group is said alcohol or amide, and further including a water molecule associated with said tetraazacyclododecane ligand and said paramagnetic metal ion, said water molecule having a residence lifetime at about 298°K, $\tau_M^{298}$, of between about 1 and about 100 microseconds.

4. The magnetic resonance contrast agent compound as recited in claim 2, wherein said R$^2$ group is said carboxyl, and further including a water molecule associated with said tetraazacyclododecane ligand and said paramagnetic metal ion, said water molecule having a residence lifetime at about 298°K, $\tau_M^{298}$, of between about 10 and about 100 nanoseconds.

5. The magnetic resonance contrast agent compound as recited in claim 1, wherein said chirality of said carbon atoms C' is controlled to provide said three or more of said pendant arms with a Δ or Λ orientation, and wherein a chirality of a ring carbon bonded to said one or more of substituents R$^6$ provides said macrocylic ring with an opposite orientation, λλλλ or δδδδ, respectively, said tetraazacyclododecane ligand thereby having a monocapped square antiprism coordination geometry.

6. The magnetic resonance contrast agent compound as recited in claim 5 wherein said R$^2$ group is said alcobol or amide, and further including a water molecule associated with said tetraazacyclododecane ligand and said pararnagnetic metal ion, said water molecule having a residence lifetime at about 298°K, $\tau_M^{298}$, of berween about 10 and about 5000 microseconds.

7. The magnetic resonance contrast agent compound as recited in claim 5, wherein said R$^2$ group is said carboxyl, and further including a water molecule associated with said tetrcyclododecane ligand and said paramagnetic metal ion, said water molecule having a residence lifetime at about 298°K, $\tau_M^{298}$, of between about 100 and about 500 nanoseconds.

8. The magnetic resonance contrast agent compound as recited in claim 5, wherein said R$^2$ group is said phosphonate or said phosphinate, and further including a water molecule associated with said tet azacyclododecane ligand and said paramagnetic metal ion, said water molecule having a residence lifetine at about 298°K, $\tau_M^{298}$, of between about 10 and about 100 nanoseconds.

9. The magnetic resonance contrast agent compound as recited in claim 1, wherein said R$^1$ is a methyl group, said R$^2$ is said carboxvl, and said R$^6$ is a para-aminobenzyl group and said paramagnetic metal ion is Gd$^{3+}$.

10. The magnetic resonance contrast agent compound as recited in claim 1, further including a water molecule associated with said tetraazacyclododecane ligand said water molecule having residence lifetime at about 298°K, $\tau_M^{298}$,of about 15 nanoseconds.

11. The magnetic resonance contrast agent compund as recited in claim 1, wherein at least one of said one or more of substituents R$^6$ include a functional group selected from the group consisting of:

amino groups;

carboxylates;

isothiocyanates; and maleiimdes; and a carrier component conjugated to said functional group.

12. The magnetic resonance contrast agent compound as recited in claim 1, wherein said paramagnetic metal is a lanthanide ion.

* * * * *

UNITED STATES PATENT AND TRADEMARK OFFICE
CERTIFICATE OF CORRECTION

PATENT NO. : 7,012,140 B1
APPLICATION NO. : 10/619362
DATED : March 14, 2006
INVENTOR(S) : A. Dean Sherry, Mark Woods and Zoltan Kovacs It is certified that error appears in the above-identified patent and that said Letters Patent is hereby corrected as shown below:

Column 4, lines 14-17 should appear as follows:

FIGURE 3A and FIGURE 3B illustrates exemplary $^1$H NMR spectra of [Eu(S-RRRR-NO₂BnDOMA)] [Eu(S-RRRR-NO$_2$BnDO$\underline{T}$MA)] and [Eu(S-SSSS-NO$_2$BnDOTMA)], respectively, produced according to the present; and Column 5, lines 60-67 through and including Column 6, lines 1-3 should appear as follows:

For example, when the three or more pendant arm carbon atoms C' have Δ orientations and the chirality of the one or more $R^6$-substituted ring carbons is selected such that the macrocyclic ring has an identical (δδδδ) orientation, then the tetraazacyclododecane ligand has a capped twisted square antiprism configuration. Or, when the three or more pendant arm carbon atoms C' have Λ orientations arid $\underline{and}$ the chirality of the one or more ring carbons is selected such that the macrocyclic ring has a (λλλλ) orientation, then the tetraazacyclododecane ligand again has a capped twisted square antiprism configuration.

Column 8, lines 61-67 through Column 9, lines 1-11 should appear as follows:

In certain preferred embodiments of the method 100, the contrast agent further includes a carrier component, conjugated to one or more of the functionalized substituents $R^6$, as discussed above. In certain embodiments of the present invention, the CA includes at least one and up to twenty of the tetraazacyclododecane ligands. Such ligands may be covalently or noncovalently bonded to a carrier component, such as described above, comprising a portion of the contrast agent. Collecting several such ligands, and associated metal ions and bound water molecules, allows a larger effective magnetic resonance signal to be achieved at lower concentrations of contrast agent. In certain such embodiments, where the water molecule (H$_2$O) associated with the tetraazacyclododecane ligand has a $\tau_M^{298}$, of between about 10 and about 100 nanoseconds, the water molecule associated with a contrast agent that further includes a carrier component has a relativity $\underline{relaxivity}$ at 298°C, $r_1^{298}$, of at least about 50 mM$^{-1}$ s$^{-1}$.

UNITED STATES PATENT AND TRADEMARK OFFICE
CERTIFICATE OF CORRECTION

PATENT NO.        : 7,012,140 B1
APPLICATION NO.   : 10/619362
DATED             : March 14, 2006
INVENTOR(S)       : A. Dean Sherry, Mark Woods and Zoltan Kovacs It is certified that error appears in the above-identified patent and that said Letters Patent is hereby corrected as shown below:

Column 11, lines 59-67 through Column 12, lines 1-5 should appear as follows:

The two complexes [Gd(S-RRR- NO$_2$BnDOTMA)]⁻ and [~~Gd(s-ssss-N)$_2$BaDOTMA)~~]⁻ [Gd(S-SSSS-NO$_2$BnDOTMA)]⁻ have substantially different $1/T_2$ - temperature profiles, indicating substantially different water exchange rat~~es. The profile for [Gd(S-RRRR~~-N)$_2$BnDOTMA)]⁻ [Gd(S-RRRR- NO$_2$BnDOTMA)]⁻, rises, maximizes and then falls away with increasing temperature, indicative of fairly slow water exchange. In contrast, the profile for [Gd(S-SSSS-NO$_2$BnDOTMA)], did not reach a maximum within the temperature range study, indicative of a more rapid water exchange. The values of $\tau_M^{298}$ obtained by fitting procedures, well known to those skilled in the art, to profiles such as depicted in FIGURE 4, are summarized in TABLE 2. Also shown in TABLE 2 are the relaxivities of water molecules associated with these ~~somers~~ isomers at 25 and 37 °C.

Claim 1 should appear as follows:

The following clerical or typographical error was noted in Claim 1:

1. A magnetic resonance contrast agent compound comprising:

a ~~tetraacyclododecane~~ tetraazacyclododecane ligand having a general structural formula as follows:

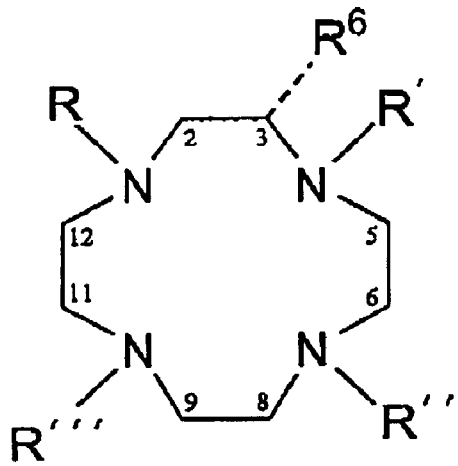

UNITED STATES PATENT AND TRADEMARK OFFICE
CERTIFICATE OF CORRECTION

| | | |
|---|---|---|
| PATENT NO. | : 7,012,140 B1 | |
| APPLICATION NO. | : 10/619362 | |
| DATED | : March 14, 2006 | |
| INVENTOR(S) | : A. Dean Sherry, Mark Woods and Zoltan Kovacs | |

It is certified that error appears in the above-identified patent and that said Letters Patent is hereby corrected as shown below:

(claim 1 continued)

and comprising a ~~macrocylic~~ macrocyclic ring and wherein pendant arms R, R', R'' and R''' attached to a ring nitrogen have the general formula: $-C'HR^1R^2$ and for three or more of said pendant arms a chirality of said carbon atoms C' are identical for each of said three or more pendant arms, said $R^1$ are groups larger than hydrogen, and said $R^2$ is selected from the ~~goup~~ group consisting of:

an alcohol ($-CH_2OH$);

amides ($-CONR^3R^4$, where $R^3$ and $R^4$ are organic groups);

a carboxylate (-COOH);

phosphinates ($-PO_2HR^5$, where $R^5$ is an organic group); and a phosphonate ($-PO(OH)_2$); and wherein one or more of substituents $R^6$ is a group larger than a methyl group and is located on one or more ring carbons; and a ~~paramagetic~~ paramagnetic metal ion coordinated to said tetraazacyclododecane ligand.

The correction to claim 1 is fully supported in Column 12, lines 48, 61 and 67 and Column 13, line 11.

Claim 5 should appear as follows:

5. The magnetic resonance contrast agent compound as recited in Claim 1, wherein said chirality of said carbon atoms C' is controlled to provide said three or more of said pendant arms with a Δ or Λ orientation, and wherein a chirality of a ring carbon bonded to said one or more of substituents $R^6$ provides said ~~macrocylic~~ macrocyclic ring with an opposite orientation, λλλλ or δδδδ, respectively, said tetraazacyclododecane ligand thereby having a monocapped square antiprism coordination geometry.

The correction to claim 5 is fully supported in Column 13, line 41.

UNITED STATES PATENT AND TRADEMARK OFFICE
CERTIFICATE OF CORRECTION

| | | |
|---|---|---|
| PATENT NO. | : 7,012,140 B1 | |
| APPLICATION NO. | : 10/619362 | |
| DATED | : March 14, 2006 | |
| INVENTOR(S) | : A. Dean Sherry, Mark Woods and Zoltan Kovacs | |

It is certified that error appears in the above-identified patent and that said Letters Patent is hereby corrected as shown below:

Claim 6 should appear as follows:

6. The magnetic resonance contrast agent compound as recited in Claim 5, wherein said $R^2$ group is said ~~alcobol~~ alcohol or amide, and further including a water molecule associated with said tetraazacyclododecane ligand and said ~~pararnagnetic~~ paramagnetic metal ion, said water molecule having a residence lifetime at about 298°K, $\tau_M^{298}$, of ~~berween~~ between about 10 and about 5000 microseconds.

The correction to claim 6 is fully supported in Column 14, line 2, 4, 5 and 6.

Claim 7 should appear as follows:

7. The magnetic resonance contrast agent compound as recited in Claim 5, wherein said $R^2$ group is said carboxyl, and further including a water molecule associated with said ~~tetrcyclododecane~~ tetraazacyclododecane ligand and said paramagnetic metal ion, said water molecule having a residence lifetime at about 298°K, $\tau_M^{298}$, of between about 100 and about 500 nanoseconds.

The correction to claim 7 is fully supported in Column 14, line 11.

Claim 8 should appear as follows:

8. The magnetic resonance contrast agent compound as recited in Claim 5, wherein said $R^2$ group is said phosphonate or said phosphinate, and further including a water molecule associated with said ~~tet azacyclododecane~~ tetraazacyclododecane ligand and said paramagnetic metal ion, said water molecule having a residence ~~lifetine~~ lifetime at about 298°K, $\tau_M^{298}$, of between about 10 and about 100 nanoseconds.

The correction to claim 8 is fully supported in Column 14, lines 18 and 20.

UNITED STATES PATENT AND TRADEMARK OFFICE
CERTIFICATE OF CORRECTION

PATENT NO. : 7,012,140 B1
APPLICATION NO. : 10/619362
DATED : March 14, 2006
INVENTOR(S) : A. Dean Sherry, Mark Woods and Zoltan Kovacs It is certified that error appears in the above-identified patent and that said Letters Patent is hereby corrected as shown below:

Claim 9 should appear as follows:

9. The magnetic resonance contrast agent compound as recited in Claim 1, wherein said $R^1$ is a methyl group, said $R^2$ is said ~~carboxyl~~ carboxyl, and said $R^6$ is a para-aminobenzyl group and said paramagnetic metal ion is $Gd^{3+}$.

The correction to claim 9 is fully supported in Column 14, line 24.

Claim 11 should appear as follows:

11. The magnetic resonance contrast agent ~~compund~~ compound as recited in Claim 1, wherein at least one of said one or more of substituents $R^6$ include a functional group selected from the group consisting of:

amino groups;

carboxylates;

isothiocyanates; and maleiimdes; and a carrier component conjugated to said functional group.

The correction to claim 11 is fully supported in Column 14, line 31.

Signed and Sealed this

Twelfth Day of February, 2008

JON W. DUDAS
*Director of the United States Patent and Trademark Office*